(12) United States Patent
Siess et al.

(10) Patent No.: US 10,195,414 B2
(45) Date of Patent: Feb. 5, 2019

(54) LOCKABLE QUICK COUPLING

(75) Inventors: Thorsten Siess, Würselen (DE); Gerd Spanier, Aachen (DE)

(73) Assignee: ABIOMED EUROPE GMBH, Aachen (DE)

( * ) Notice: Subject to any disclaimer, the term of this patent is extended or adjusted under 35 U.S.C. 154(b) by 854 days.

(21) Appl. No.: 13/499,207

(22) PCT Filed: Sep. 23, 2010

(86) PCT No.: PCT/EP2010/064059
§ 371 (c)(1),
(2), (4) Date: Apr. 24, 2012

(87) PCT Pub. No.: WO2011/039101
PCT Pub. Date: Apr. 7, 2011

(65) Prior Publication Data
US 2012/0209057 A1    Aug. 16, 2012

(30) Foreign Application Priority Data

Sep. 30, 2009 (DE) .................. 10 2009 047 844

(51) Int. Cl.
*A61M 39/10* (2006.01)
(52) U.S. Cl.
CPC . *A61M 39/1011* (2013.01); *A61M 2039/1033* (2013.01); *A61M 2039/1066* (2013.01)

(58) Field of Classification Search
CPC ...... A61M 39/1011; A61M 2039/1033; A61M 2039/1066
See application file for complete search history.

(56) References Cited

U.S. PATENT DOCUMENTS

| | | | |
|---|---|---|---|
| 3,442,288 A | 5/1969 | Scaramucci | |
| 4,148,459 A * | 4/1979 | Martinez | F16L 37/40 251/149.6 |
| 4,433,973 A | 2/1984 | Kurtz et al. | |
| 5,087,086 A * | 2/1992 | Snedeker | 285/361 |
| 5,456,676 A | 10/1995 | Nelson et al. | |
| 5,738,143 A * | 4/1998 | Faughn | 137/614.03 |
| 6,722,705 B2 * | 4/2004 | Korkor | 285/332 |
| 2007/0213690 A1 | 9/2007 | Phillips | |

FOREIGN PATENT DOCUMENTS

| | | |
|---|---|---|
| CA | 2566600 | 9/2009 |
| DE | 10321309 | 1/2004 |
| EP | 0633038 | 1/1995 |
| EP | 1331020 | 7/2003 |
| GB | 190906216 | * 7/1909 |

* cited by examiner

*Primary Examiner* — James M Hewitt, II
(74) *Attorney, Agent, or Firm* — White & Case LLP

(57) ABSTRACT

A simply lockable quick coupling for releasably connecting a hose to an implantable apparatus, comprises a first attachment piece that can be connected to the hose and a second attachment piece that can be connected to the apparatus, wherein the attachment pieces can be rotated relative to each other in the locked state.

7 Claims, 3 Drawing Sheets

LOCKABLE QUICK COUPLING

RELATED APPLICATIONS

Figure 1:
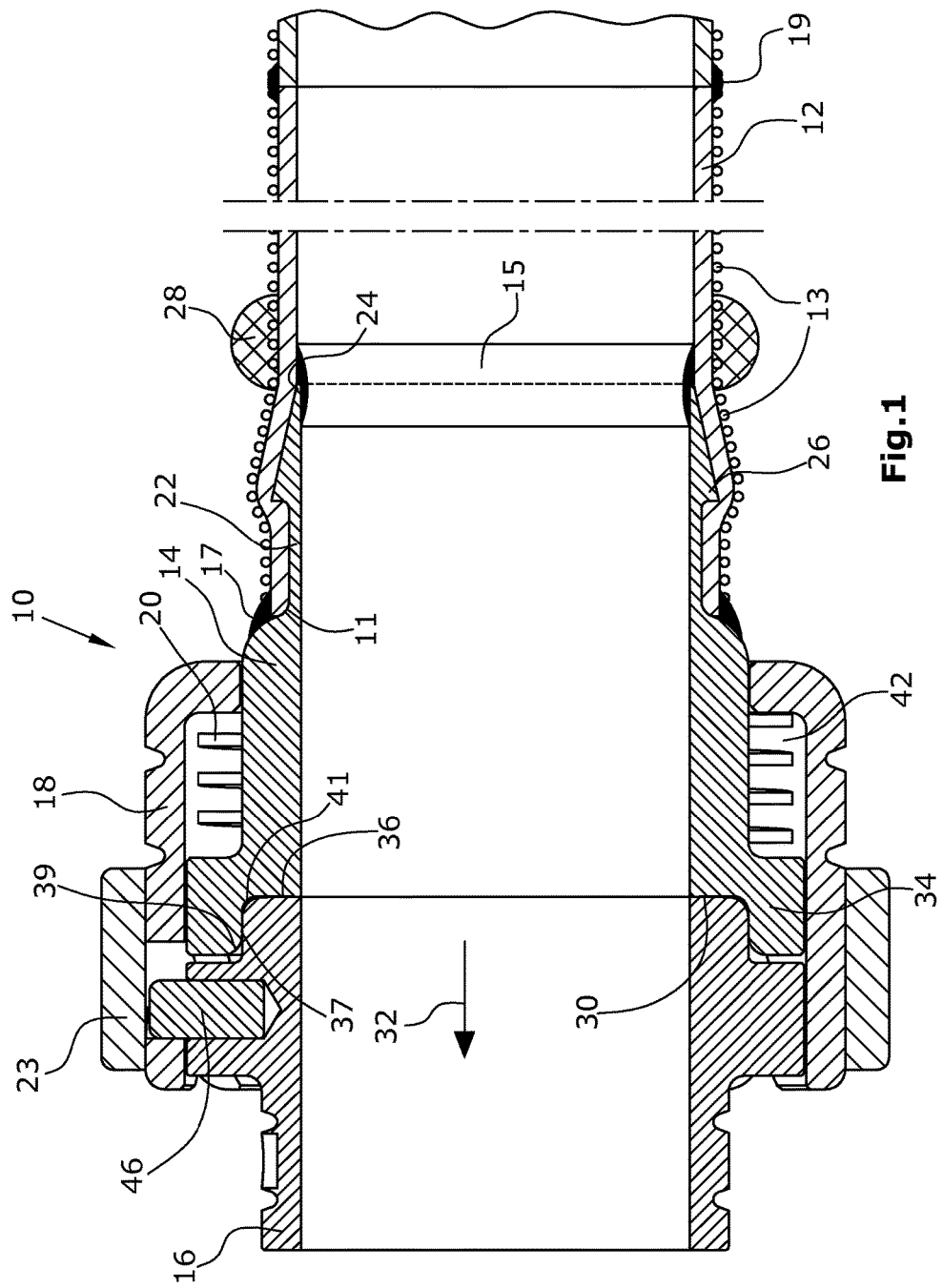

This application is a U.S. national phase of PCT/EP2010/064059, filed Sep. 23, 2010, which claims priority from Germany Application Serial No. 102009047844.2, filed Sep. 30, 2009.

The invention relates to a lockable quick coupling for releasably connecting a hose to an implantable apparatus.

Implantable apparatus are typically medical auxiliary apparatus such as e.g. blood pumps to implanted into a patient's body and to be connected to a hose conveying a liquid. In case of a blood pump, one end of the hose typically is to be connected to an artery and the other end is to be connected to the blood pump. When connecting the hose to the implanted apparatus, a difficulty resides in that the forces involved in this process might cause damage to the connection between the hose and the artery.

From U.S. Pat. No. 7,273,446 B2, a blood pump is known which works anticyclically relative to the pulsation of the heart. In such a counterpulsatile blood pump, referred to as a CPD ("counter pulsation device"), the hose conveying the blood will be fixedly sewed to the subclavia, and the pump will be implanted into the right-hand cardiac pacemaker pocket in the patient's breast region. The pump is operative to suction the quantity of blood ejected by the heart during the systole, thus reducing the force to be generated by the heart muscle. After closure of the aortic valve, during the diastole, the CPD will pump the previously received blood quantity into the artery. When implanting a CPD, the pump will have to be connected to the hose sewed to the subclavia. In the process, the hose will transmit torsional forces and other forces to the connecting seam with the subclavia. For this reason, the connecting of the hose and the pump to each other must be performed with utmost caution so as to avoid damage to the connecting seam at the subclavia. Further, the connection has to be produced without ingress of air and without visible transition edges.

It is an object of the invention to facilitate the connecting of a hose to an implantable apparatus.

The solution offered by the invention is a lockable quick coupling for releasably connecting a hose to an implantable apparatus. The quick coupling comprises a first attachment piece which is connectable to the hose and a second attachment piece which is connectable to the apparatus. The two attachment pieces can be releasably locked to each other and can be rotated relative to each other in the locked state.

The two attachment pieces can be connected to each other in a simple manner, e.g. after the apparatus has been implanted into the patient and the hose has been sewed to an artery of the patient. When connecting the two attachment pieces, smaller forces have to be applied than before. In case of a CPD, lesser forces will be acting onto the hose, and the danger of damage caused to the connecting seam to the subclavia is reduced. Particularly, the connecting between the first attachment piece and the hose can be established already prior to delivery so that, for connecting the hose to the apparatus, the surgeon will merely have to connect the two attachment pieces to each other. Since, in their locked state, the two attachment pieces can be rotated relative to each other, the danger of torsion of the hose during the establishing of the connection to the apparatus is reduced or can at least be corrected directly after the connecting. Further, the quick coupling allows for particularly small constructional dimensions with small additional diameter, small wall thickness and short size. The small size of the quick coupling is of particular importance in order to allow the connection of the hose to the apparatus to be established within limited space during implantation. Particularly, the hose (graft) can be guided toward the pump in a radius.

Preferably, the attachment pieces are formed to have annular contact faces which fit onto each other, wherein each contact face encloses a passage through the attachment piece so that, by locking the attachment pieces to each other, the contact faces will be pressed together and will automatically form a sealing connection. Particularly in case of a counterpulsatile blood pump, the high pressures involved make it important to have a well-sealing connection. In this regard, it is advantageous if a radially outer peripheral region of each contact face is receding relative to a sealing inner contact region by an angle α of a few degrees and preferably less than one degree. Thereby, in the locked state, the contact faces will contact each other only in the inner contact region so that, in the inner contact region bordering on the passage, the surface pressure will be increased and the sealing effect will be improved. Since the highest surface pressure will be achieved in the region of the blood-conducting passage, the necessity for a separate sealing element, e.g. in the form of a sealing ring, is obviated.

Preferably, one attachment piece, particularly the first attachment piece connectible to the hose, is enclosed by a retaining nut which is lockable in such a manner with the other, second attachment piece connectible to the apparatus that a cavity is formed between said other attachment piece and the retaining nut. In said cavity, there is held said one, first attachment piece which is connectible particularly to the hose, while the retaining nut can be locked to said other attachment piece. Said one attachment piece enclosed by the retaining nut is connected to said second attachment piece with the aid of the retaining nut, and within the cavity, it can be rotated as desired relative to said other attachment piece.

Within the cavity, a spring can be provided for exerting a force from the retaining nut to said one attachment piece in the direction of said other attachment piece. In the locked state, the attachment piece enclosed by the retaining nut is pressed by the spring against said other attachment piece in the axial direction, while the two attachment pieces can be rotated relative to each other. In order to achieve an equally distributed pressure onto the mutually pressed contact faces in the locked state, the spring preferably is a sinuous spring which in the compressed, locked state will exert a maximum pressure. The danger of the two attachment pieces becoming wedged is reduced, and the sealing effect is distributed in a uniform manner along the periphery.

Said first attachment piece connectible to the hose preferably comprises a collar, provided with a sharp end edge, onto which the hose will be mounted. The sharp end edge allows for a nearly stepless transition between the hose and the attachment piece so as to reduce the risk of agglomeration of blood. On its outer side, the collar is provided with a step for securing the mounted hose in the manner of a barb against sliding off the attachment piece. The connection between the sharp-edged first attachment piece and the hose can be established and sealed, with the required diligence, already prior to delivery of the quick coupling, thus reducing the risk of injury to the surgeon and the risk of gaps when establishing the connection.

For locking, there is preferably provided a bayonet-type lock between the retaining nut and the second attachment piece, wherein the retaining nut can comprise a protective ring covering the bayonet-type lock, so as to reduce the risk of injury to the surgeon when establishing the connection, or to reduce the intrusion of glove material. With the aid of the bayonet-type lock, the connection can be achieved in a releasable and simple manner by shifting the two attachment pieces onto each other and subsequently rotating them relative to each other, while the rotating movement during the closing of the bayonet-type lock will not be transmitted to the hose and thus not to the region of a possible seam for connection to a vessel of the patient. Preferably, the two attachment pieces, the retaining nut and the implantable spring are made of titanium for thus creating a stable and light-weighted quick coupling which will not corrode by blood. The protective ring is preferably made of transparent plastic with high friction so that an surgeon, even when wearing surgical gloves, can safely grip the ring and rotate it for locking.

An exemplary embodiment will be explained in greater detail hereunder with reference to the Figures.

Figure 2:
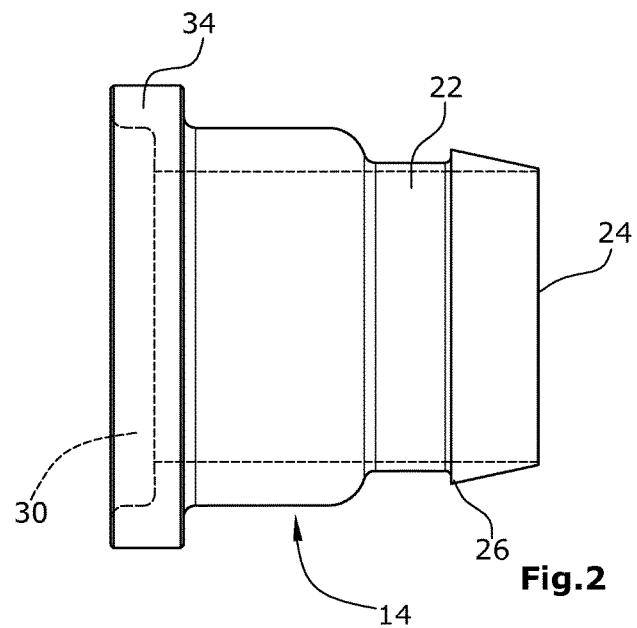
Figures 3, 4:
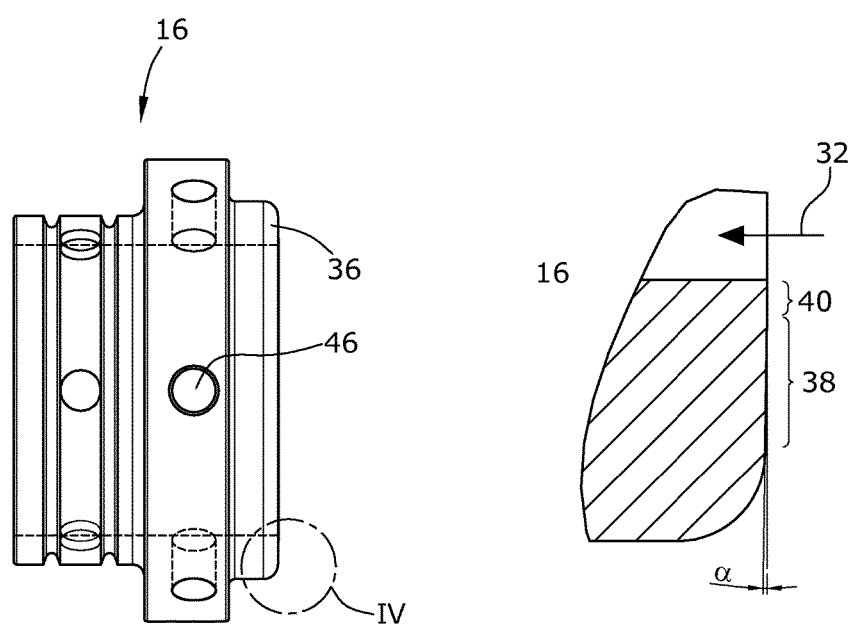
Figure 5:
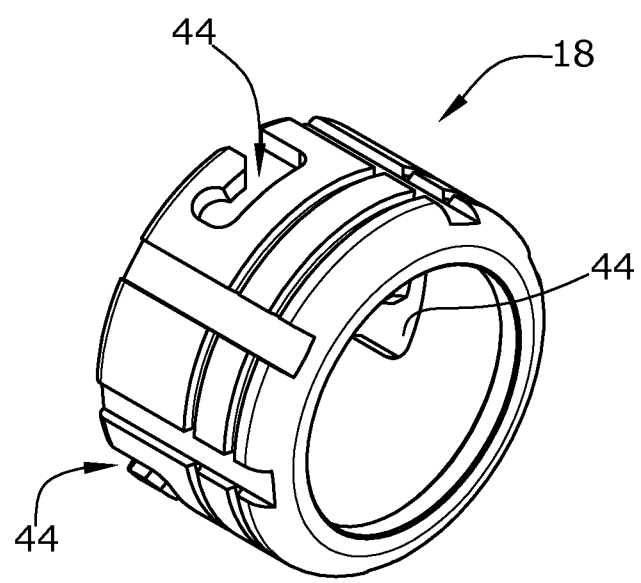

In the Figures,

FIG. 1 is a longitudinal sectional view of the quick coupling of the invention with attached hose, FIG. 2 is a lateral view of a first attachment piece according to said embodiment, FIG. 3 is a lateral view of a second attachment piece according to said embodiment, FIG. 4 is a longitudinal sectional view of the region IV in FIG. 3, and FIG. 5 is a perspective view of retaining nut according to said embodiment.

The quick coupling 10 comprises the first attachment piece 14, connectible to the hose 12, the second attachment piece 16 connectible to the implantable apparatus, the retaining nut 18, the spring 20 and the protective ring 23.

FIG. 1 shows the first attachment piece 14 with the hose 12 shifted thereonto. For this purpose, the first attachment piece 14 comprises a projecting cylindrical collar 22 whose surrounding end edge 24 terminates with an acute shape so that, in the transition region between collar 22 and hose 12, there is formed no edge distinctly protruding into the hose lumen and entailing the risk of blood coagulation thereon. On its outer side, collar 22 is provided with a surrounding step 26 forming a projection toward the second attachment piece 16 and obliquely tapering toward the end edge 24. In this manner, hose 12, which is thermally shrink-fitted onto collar 22, is protected by said step 26 in the manner of a barb against sliding out of place. A nitinole spiral 13 encloses the hose 12 proximally and distally relative to end edge 24, and prevents a widening of the hose 12, which could cause the hose 12 to slide off from the first attachment piece 14 and to become damaged by friction on the sharp end edge 24. Proximally on the first attachment piece 14, the nitinole spiral 13 will be covered by a fatigue-endurable and biocompatible synthetic adhesive (epoxy) 17. In the process, the abutment edge of hose 12 will be completely encapsulated toward the attachment piece 14 and be secured against widening.

On the distal end of the nitinole spiral 13, the last helix of the nitinole spiral 13 will be guided back to the second-to-last helix of the nitinole spiral 13. There, the two helices of the nitinole spiral 13 will be guided in parallel over a short distance and be laser-welded onto the upper and the lower side. Then, the complete region of the distal end of the nitinole spiral 13 will be encapsulated, over two helices, by fatigue-endurable and biocompatible synthetic adhesive. As a result, an acute end of the nitinole spiral 13 is prevented, and a perforation or puncture of hose 12 is avoided.

Hose 12 will be bonded to attachment piece 14 by a fatigue-endurable adhesive, and the end edge 24 will be covered by a fatigue-endurable and biocompatible synthetic adhesive (epoxy) 15 for full elimination of blood from edge 24.

On its distal end opposite to end edge 24, the first attachment piece 14 comprises a contact face 30 for contacting the second attachment piece 16. The contact face 30 has an annular shape and encloses a passage 32 of the cylindrical lumen passing through the two attachment pieces 14,16. Externally, contact face 30 is delimited by a cylindrical holding edge 34 projecting in the distal direction and toward the outside. The inner diameter of holding edge 34 is slightly larger than the outer diameter at the proximal end of the second attachment piece 16 so that the holding edge 34 can be shifted onto the second attachment piece 16 and will grip around the proximal end of the second attachment piece 16.

The proximal end of the second attachment piece 16 comprises an annular contact face 36 enclosing the passage 32 on the outside. The two contact faces 30 and 36 are shaped to fit onto each other wherein, respectively, an outer peripheral region 38 of each contact face 30,36, as shown in FIG. 4, is receding relative to an inner contact region 40 by an angle a such that the contact faces 30,36 in the mutually pressed state shown in FIG. 1 contact each other only in the inner contact region 40 and are spaced from each other in the outer peripheral region 38. Thereby, the surface pressing in the inner contact region 40 is relatively high, and there is effected a uniformly surrounding sealing on the basis of a press fit without the need for an additional sealing element such as e.g. a sealing ring. In the region 37, the two attachment pieces 14 and 16 are radially adapted by clearance fit within each other, so that the two parts are easily joined while the maximal radial offset will still be at a minimum. Consequently, there will be no abutting edge for blood whereon blood components could deposit. The strip of the clearance fit in the region 37 is short and on both ends is provided with exactly adjusted radii 41/39, allowing the attachment pieces 16 and 14 to be tilted relative to each other for venting. In this case, the band will serve as an abutment edge and thus will facilitate the joining. Thus, liquid can be applied from above into the generated slit/gap while the parts can be joined without inclusion of air.

The first attachment piece 14 is on the outside enclosed by the retaining nut 18. The proximal end of the retaining nut 18, in FIG. 1 being the right-hand end, has an inner diameter which is smaller than the outer diameter of holding edge 34. In this manner, a cavity 42 for the spring 20 is provided between the retaining nut 18 and the first attachment piece 14. The retaining nut 18 can be shifted, in the proximal direction, fully past the first attachment piece 14 and in the distal direction will be held by the holding edge 34. Between the holding edge 34 and the proximal region with reduced inner diameter of retaining nut 18, the spring 20, when the retaining nut 18 is shifted, will be pressed together in the distal direction—the left-hand direction in FIG. 1—and will exert a spring pressure onto the retaining nut 18 in the proximal direction relative to the first attachment piece 14. Spring 20 is a sinuous spring for generating a spring pressure which is distributed in a uniform manner along the periphery.

As shown in FIG. 5, the retaining nut 18 comprises, on its distal end which in FIG. 5 is the left-hand end, three circumferentially distributed longitudinal holes 44 of a bayonet-type lock. Said hook-shaped holes 44 each engage a corresponding knob 46 radially projecting from the second attachment piece 16, so that the bayonet-type lock comprising said longitudinal holes 44 and said knobs 46 can be locked by an insertion-and-rotation movement of the retaining nut 18 relative to the second attachment piece 16 and will lock the retaining nut 18 to the second attachment piece 16. In the locked state shown in FIG. 1, the spring 20 presses the first attachment piece 14 against the second attachment piece 16 while the inner contact regions 40 of the contact faces 30,36 maintain a sealing press fit between them.

In the region of the hook-shaped longitudinal holes 44, the retaining nut 18 is enclosed by a protective ring 23, not shown in FIG. 5, which is made of transparent plastic and, as shown in FIG. 1, covers the bayonet-type lock on the outside. It is thus avoided that, while the quick coupling 10 is being locked, a surgical glove of a surgeon may happen to enter the bayonet-type lock and to get clamped therein. Further, the plastic ring will offer a good grip even to surgical gloves. The ring 28 (preferably made of silicon) shown in FIG. 1 serves as a retaining ring for the retaining nut 18, thus preventing that the latter can escape in the direction of the seam side prior to the jointing process.

In the exemplary embodiment, the implantable apparatus to be connected to hose 12 is a counterpulsatile blood pump (CPD), not shown in the Figures. Hose 12 is an arterial graft whose proximal end, located opposite to the quick coupling 10 will be tightly sewed to an artery ascending from the heart, typically the subclavia, so that the hose 12 will have arterial blood flowing therethrough. In this regard, the quick coupling makes it possible to first produce the seam between the hose 12 and the subclavia during an operation, and then, in a simple manner, to connect the end of the hose 12 opposite the subclavia to the blood pump, without hazardous pulling, pressing or torsional forces being exerted between the hose 12 and the subclavia. The two attachment pieces 14,16, the spring and the retaining nut 18 are made of titanium, and the hose 12 is made of a relatively elastic and bendable material (e.g. EPTFE).

The connection between the first attachment piece 14 and the hose 12 can be produced, with the required care, already beforehand in a laboratory so that, with the aid of a suitable sealing, it will be precluded that the sharp end edge 24 might pose a risk to the surgeon or to the hose 12 when the connection is being established. Herein, the connection between the hose 12 and the first attachment piece 14 can be produced under quality control by the manufacturer and independently of the surgeon. During implantation, the surgeon merely has to lock the bayonet-type lock, without thereby having any influence on the leak-tightness of the connection.

The invention claimed is:

1. A lockable quick coupling for releasably connecting a hose to an implantable apparatus, comprising a first attachment piece which can be connected to the hose and having a first annular contact face, and a second attachment piece which can be connected to the apparatus and having a second annular contact face, wherein the attachment pieces can be locked to each other to define a locked state and rotated relative to each other while remaining in the locked state, the first and second annular contact faces being pressed together and forming a sealing connection in said locked state, the sealing being obtained without the necessity for a separate sealing element in the form of a sealing ring;

wherein:
the quick coupling comprises a bayonet-type lock with a spring;
the bayonet-type lock comprises a retaining nut enclosing one of the first and second attachment pieces;
said bayonet-type lock being operable to lock the retaining nut to the other of the first and second attachment pieces in such a manner that a cavity for receiving said one of the first and second attachment pieces is formed between the retaining nut and the other of the first and second attachment pieces;
said spring is located in said cavity, and is provided for exerting a force from the retaining nut to said one attachment piece in a direction towards said other attachment piece;
the annular contact face of said one attachment piece is delimited by a cylindrical holding edge projecting in an axial direction towards the other attachment piece beyond the annular contact face of said one attachment piece and projecting outward in a radial direction; and
in said locked state, said cylindrical holding edge is contained in said cavity.

2. The quick coupling according to claim 1, wherein the annular contact faces fit onto each other, each of said contact faces enclosing a passage through the attachment piece.

3. The quick coupling according to claim 2, wherein each of said annular contact faces includes:
a sealing inner contact region; and
a radially peripheral region outside the sealing inner contact region;
wherein the radially peripheral regions of the first and second attachment pieces are shaped to prevent contact with each other when the first and second attachment pieces are in the locked state.

4. The quick coupling according to claim 1, wherein said spring is a sinuous spring.

5. The quick coupling according to claim 1, wherein the first attachment piece for the hose comprises a cylindrical collar having a sharp end edge and having a step which is effective, in the manner of a barb, to secure the hose from sliding off.

6. The quick coupling according to claim 1, wherein the quick coupling comprises a protective ring covering said bayonet-type lock.

7. The quick coupling according to claim 1, wherein the two attachment pieces are made of titanium and all other elements of the quick coupling are made of titanium and/or from stainless steel which is implantable into synthetic materials.

* * * * *